United States Patent [19]

Ninomiya et al.

[11] Patent Number: 4,883,802
[45] Date of Patent: Nov. 28, 1989

[54] 4-PIPERIDINECARBOXAMIDE DERIVATIVES

[75] Inventors: Kunihiro Ninomiya; Ken-Ichi Saito, both of Machida; Shuji Morita; Akihiro Tobe, both of Yokohama; Issei Nitta, Machida, all of Japan

[73] Assignee: Mitsubishi Kasei Corporation, Tokyo, Japan

[21] Appl. No.: 243,322

[22] Filed: Sep. 9, 1988

[30] Foreign Application Priority Data

Sep. 16, 1987 [JP] Japan .................................. 62/231591

[51] Int. Cl.⁴ .................. A61K 31/395; C07D 401/12; C07D 401/14
[52] U.S. Cl. .................................. 514/278; 514/320; 514/326; 546/15; 546/201; 546/208
[58] Field of Search .......................... 546/201, 208, 15; 514/278, 320, 326

[56] References Cited

U.S. PATENT DOCUMENTS 4,341,790 7/1982 Betzing et al. ...................... 545/544

FOREIGN PATENT DOCUMENTS 0115472 8/1984 European Pat. Off. ............. 548/546
1588082 4/1981 United Kingdom ................. 546/208

Primary Examiner—Robert T. Bond
Attorney, Agent, or Firm—David G. Conlin

[57] ABSTRACT

A novel 4-piperidinecarboxamide derivatives represented by the general formula (I):

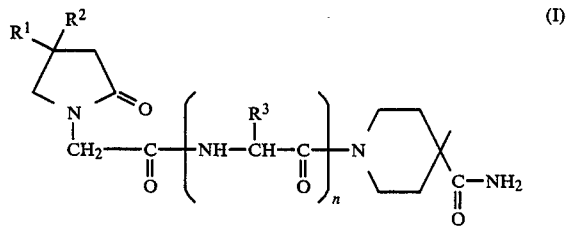

wherein each $R^1$ and $R^2$ represents a hydrogen atom, or $R^1$ together with $R^2$ represents a cyclopentanespiro or cyclohexanespiro group; $R^3$ represents a hydrogen atom, an alkyl group having 1 to 4 carbon atoms, an aralkyl group or an indolylalkyl group; and n is an integer of 1 or 2;

is disclosed herein. The novel compound is useful as the agent for improving the impaired brain fuction.

3 Claims, No Drawings

4-PIPERIDINECARBOXAMIDE DERIVATIVES

FIELD OF THE INVENTION

The present invention relates to novel 4-piperidinecarboxamide derivatives useful as agents for improving the impaired brain function.

BACKGROUND OF THE INVENTION

For the treatment of the impairment of memory by different causes such as multiple infarcted dementia, senile dementia, Alzheimer's dementia, sequelae of cerebral injury and cerebral apoplexy and the like, various agents such as cerebral vasodilators, agents for improving cerebral metabolism, nootropic agents and the like have been proposed, but the satisfactory improvement could not be obtained by any of these agents.

As the extensive research with respect to the compounds showing the satisfactory improvement of the impaired brain function, the present inventors found that 4-piperidinecarboxamide derivatives having N-[(2-oxo-1-pyrrolidinyl)-acetyl]-peptide side chain at 1 position improve the impaired brain function.

SUMMARY OF THE INVENTION

The present invention provides the 4-piperidinecarboxamide derivatives represented by the general formula (I):

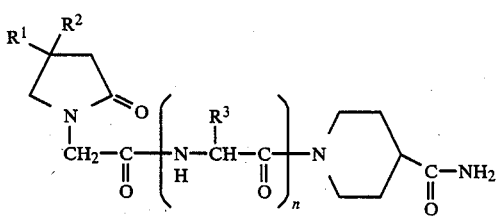

wherein each $R^1$ and $R^2$ represents a hydrogen atom, or $R^1$ together with $R^2$ represents a cyclopentanespiro or cyclohexanespiro group; $R^3$ represents a hydrogen atom, an alkyl group having 1 to 4 carbon atoms, an aralkyl group or an indolylalkyl group; and n is an integer of 1 or 2.

And, the present invention provides the pharmaceutical composition useful as the agent for improving the impaired brain function which comprises as the effective ingredient at least one of 4-piperidinecarboxamide derivatives having the general formula (I).

DETAILED DESCRIPTION OF THE INVENTION

4-Piperidinecarboxamide derivatives according to the present invention ( hereinafter referred to as "the present compounds(s)") have the general formula (I).

Both $R^1$ and $R^2$ in the general formula (I) represent hydrogen atoms. Alternatively, $R^1$ together with $R^2$ may represent a cyclopentanespiro or cyclohexanespiro group.

$R^3$ in the general formula (I) represents a hydrogen atom; an alkyl group having 1 to 4 carbon atoms such a methyl, ethyl, propyl, butyl and the like; an aralkyl group such as benzyl, phenetyl and the like; or an indolylalkyl group such as indole-3-yl-methyl, 5-hydroxyindole-3-yl-methyl and the like. Preferably, $R^3$ represents hydrogen, methyl, isopropyl, benzyl or indole-3-yl-methyl.

When $R^3$ represents the group other than hydrogen atom, the carbon atoms linked to $R^3$ is asymmetric. (L) configuration is preferable in the present invention.

n in the general formula (I) is an integer of 1 or 2.

The following compounds are exemplified as the preferable present compounds.

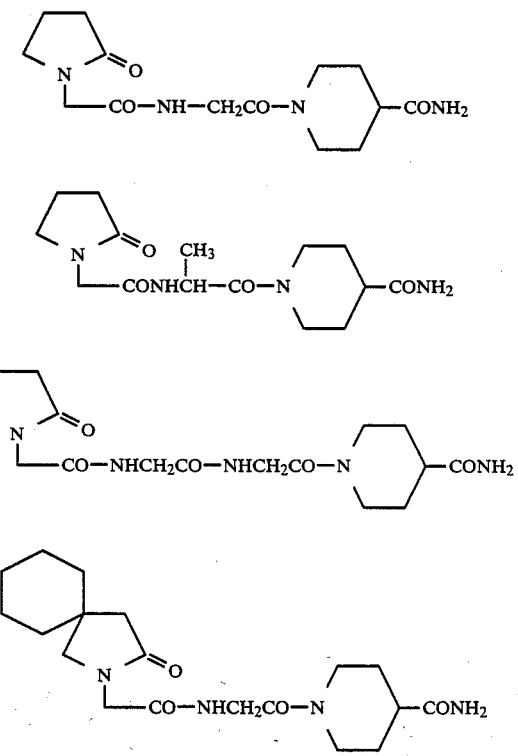

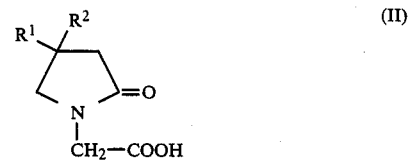

The present compounds having the general formula (I) can be prepared according to any of the known methods. For example, the following methods are illustrated.

(a) n=1

The carboxylic acid having the general formula (II)

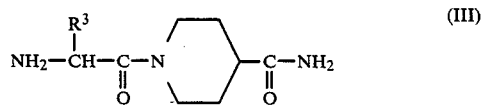

wherein $R^1$ and $R^2$ are as defined above; is subjected to the amidation with the amine having the general formula (III)

$$NH_2-CH(R^3)-C(=O)-N\underset{}{\diagup}\!\!\diagdown\!\!-C(=O)-NH_2 \quad (III)$$

wherein $R^3$ is as defined above;
in the presence of the peptide condensing agent so as to prepare the present compound.

Alternatively, the carboxylic acid having the above general formula (II) is converted to the reactive derivative thereof followed by subjecting to the amidation with the amine having the above general formula (III) so as to prepare the present compound.

(b) n=1 or 2

The carboxylic acid having the general formula (IV)

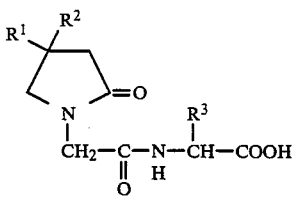

wherein $R^1$, $R^2$ and $R^3$ are as defined above; is subjected to the amidation with 4-piperidinecarboxamide or the amine having the above general formula (III) in the presence of the peptide condensing agent so as to prepare the present compound.

Alternatively, the carboxylic acid having the above general formula (V) is converted to the reactive derivative thereof followed by subjecting to the amidation with 4-piperidinecarboxamide or the amine having the above general formula (III) so as to prepare the present compound.

In the present invention, any of the conventional peptide condensing agents in the standard peptide synthesis can be used. The use of dicyclohexylcarbodiimide, carbonyldiimidazole or 1-ethoxycarbonyl-2-ethoxy-1,2-dihydroquinoline is preferable.

Examples of the reactive carboxylic acid derivatives include the mixed acid anhydride with carbonic acid monoalkylester (e.g. A-CO-O-CO-O-CH$_2$CH(CH$_3$)$_2$), carboxylic acid azide (A—CO—N$_3$), p-nitrophenyl ester

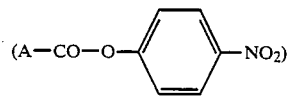

and pentachlorophenyl ester

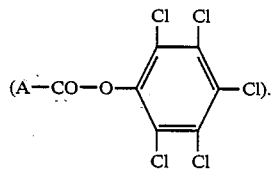

Herein, A represents

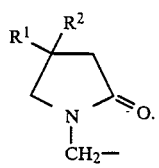

Generally, the amidation is carried out in the suitable solvent under the atmospheric pressure.

The temperature in the amidation depends on the natures of the peptide condensing agent used or the reactive carboxylic acid derivative, but generally it is in the range of −30° C. to +150° C.

The carboxylic acid having the general formula (II) which is used as the starting material for preparing the present compound is known. And, the amine having the general formula (III) and the carboxylic acid having the genneral formula (IV) can be prepared according to any of the known methods, for example, the methods described in the following reference examples.

The present compounds are pharmaceutically active and valuable. Especially, the present compounds have the protective actions against the amnesia caused by the electroconvulsive shock and against the behavioral disturbance induced by the administration of sodium nitrite.

Accordingly, the present compounds are useful as the agent for treating the impairment of memory by different causes such as multiple infarcted dementia, senile dementia, Alzheimer's dementia and the like and the sequelae of cerebral injury and cerebral apoplexy and the like. The pharmaceutical activities of the present compounds are higher than those of the so-called nootropic agents such as piracetam and aniracetam, as shown in the following test examples.

The present compound may be used alone for such a treatment. Preferably, the present compound is combined with the pharmaceutically acceptable carrier. That is, the pharmaceutical composition according to the present invention comprises at least one of the present compounds together with the pharmaceutically acceptable carrier and if necessary one or more of the known additives.

The pharmaceutical composition may have any of the conventional dosage forms depending on chemical properties including solubility of the compounds, administration route, administration plan and the like. For example, for the parenteral administration such as intramuscular injection, intravenous injection and subcutaneous injection, the present composition is used in the form of the sterile solution in which the solute such as salt, glucose and the like are added for obtaining the isotonic solution. For the oral administration, the present composition is used in the form of tablet, capsule or granule in which suitable vehicle such as starch, lactose, sucrose and the like is contained. Alternatively, the present composition may be used for the oral administration in the form of the troch such as rotula, lozenge and the like which is formed by adding sucrose, syrup, perfume, colouring material and so on and shaping. Alternatively, the present composition may be used for the oral administration in the form of the solution in which generally colouring material and perfume are added.

The dosage of the present compound is determined by the doctor considering the administration route, the nature of the compound and the conditions of the patient. Generally, the daily dosage via parenteral administration is 0.1 to 50 mg/kg, preferably 0.2 to 20 mg/kg; and the daily dosage via oral administration is 0.5 to 500 mg/kg, preferably 1 to 100 mg/kg.

EXAMPLES

The invention will now be further described by the following, non-limiting examples.

EXAMPLE 1

Preparation of 1-{N-[(2-oxo-1-pyrrolidinyl)acetyl]glycyl}-4-piperidinecarboxamide 27.8 g of (2-oxo-1-pyrrolidinyl)acetic acid was suspended in 450 ml of tetrahydrofuran, to which 27.8 g of isobutyl chloroformate at −15° C. and 20.3 g of triethylamine at −15° to −5° C. were added. After stirring at −10° to −5° C. for 15 minutes, 36.0 g of 1-glycyl-4-piperidinecarboxamide was added at −10° to −5° C. and then the reaction liquid was allowed to stand so as to rise its temperature to room temperature over 2 hours. The insoluble matter was filtered off and suspended in 500 ml of chloroform. The suspension was filtered off to obtain the crude crystal. The crude crystal was recrystallized from methanol to obtain the titled compound.

Yield=42.9 g.
Melting point=217° to 219° C.

EXAMPLES 2 to 6

The following compounds (Table 1) were prepared according to the method similar to Example 1.

TABLE 1

| Example No. | structure | melting point |
|---|---|---|
| 2 | [structure] | 179 to 181° C. |
| 3 | [structure] | amorphous solid |
| 4 | [structure] | amorphous solid |
| 5 | [structure] | amorphous solid |
| 6 | [structure] | 142 to 144° C. |

REFERANCE EXAMPLE 1

Preparation of 1-glycyl 4-piperidinecarboxamide (the starting amine used in Example 1 )

62.8 g of N-benzyloxycarbonyl glycine was dissolved in 1000 ml of tetrahydrofuran and the solution was cooled to −15° C., to which 42.3 g of isobutyl chloroformate and then 31.0 g of triethylamine were added dropwise at −15° to −5° C. and stirrd at −10° to −5° C. for 15 minutes. Next, 38.5 g of 4-piperidinecarboxamide was added while maintaining the temperature at −10° to −5° C. The reaction liquid was allowed to stand so as to rise its temperature to room temperature over 2 hours. The insoluble solid was filtered off. This solid was suspended in 500 ml of water, the suspension was stirred for 30 minutes and then the insoluble solid was filtered off. The wet solid was dissolved in 700 ml of ethanol with warming and the solution was concentrated to 200 ml at atmospheric pressure. After the concentrate was allowed to cool, 64.8 g of 1-(N-benzyloxycarbonylglycyl)-4-piperidinecarboxamide having the melting point of 164° to 166° C. was obtained. This was dissolved in 950 ml of methanol and 7 g of 5 % palladium on carbon was added thereto followed by subjecting to the catalytic hydrogenation while introducing hydrogen gas at room temperature. After 4 hours, the catalyst was filtered off and the reaction solution was concentrated to 100 ml. 250 ml of ethyl acetate was added and again the resultant solution was concentrated to 150 ml and allowed to cool so as to obtain the precipitate, which was filtered to obtain the titled compound.

Yield = 36.0 g
Melting point = 146° to 149° C.

EXAMPLE 7

Preparation of 1- {N - [(2-oxo-1-pyrrolidinyl)acetyl]-glycylglycyl}-4-piperidinecarboxamide 8.01 g of N- [(2-oxo-1-pyrrolidinyl)acetyl] glycine was dissolved in 200 ml of dimethylformamide and the solution was cooled to −15° C., to which 5.57 g of isobutyl chloroformate was added and then 4.09 g of triethylamine was added dropwise at −15° to −5° C. This was stirred at −10° to −5° C. for 15 minutes and 7.41 g of 1 glycyl-4-piperidinecarboxamide was added while maintaining the temperature at −10° to −5° C. The reaction liquid was allowed to stand so as to rise its temperature to room temperature over 2 hours. The solid filtered off was suspended in 300 ml of ethanol and the suspension was stirred for 30 minutes and filtered to obtain the solid. This solid was dissolved in the mixture of 20 ml of water and 100 ml of ethanol with heating. The resultant solution was concentrated to 30 ml under atmospheric pressure and 180 ml of ethanol was added followed by allowing to stand to form the precipitate, which was filtered to obtain the titled compound.

Yield = 12.66 g
Melting point = 225° to 227° C.

REFERENCE EXAMPLE 2

Preparation of N- [(2-oxo-1-pyrrolidinyl)acetyl] glycine (the starting carboxylic acid used in Example 7)

18.5 g of 2-oxo-1 pyrrolidinyl acetic acid was dissolved in 500 ml of dimethylformamide and the solution was cooled to −15° C., to which 18.53 g of isobutyl chloroformate was added and 13.21 g of triethylamine was added dropwise at −15° to 5° C. After stirring at −10° to −5° C. for 15 minutes, 17.04 g of glycine methyl hydrochloride was added and 13.73 g of triethylamine was added dropwise at −10° to −5° C. The reaction liquid was allowed to stand so as to rise its temperature to room temperature over 2 hours and triethylamine hydrochloride was filtered off. Dimethylformamide was distilled off under reduced pressure and the residue was purified through the chromatography on silica gel (silica gel 500 g, chloroform-1 to 2 % of methanol as the eluent). Then, the solvent was distilled off to obtain 17.97 g of N- [(2-oxo-1-pyrrolidinyl)acetyl]glycine methyl ester as the oily substance. This was dissolved in 100 ml of methanol and the solution of 4.78 g of sodium hydroxide dissolved in 150 ml of methanol was added thereto and reacted at room temperature for 12 hours. After 10 g of acetic acid was added, methanol was distilled off under reduced pressure and the residue was purified through the chromatography on silica gel (silica gel 340 g, chloroform-10 % of methanol-1 % of formic acid as the eluent). The solvent was distilled off and the residue was crystallized from tetrahydrofuran to obtain the titled compound.

Yield: 15.35 g
Melting point: 153° to 155° C.

TEST EXAMPLE 1

Effect on memory impairment

The test was carried out in accordance with the method of Susan J. Sara (Please see Psychopharmacology, 68, pages 235 to 241, 1980).

As the test device, the so-called two compartment avoidance box was used. This device comprises the lighted big box and the dark small box which is comminicated to the big box and has the metal grid floor capable of applying the foot shock.

As the experimental animal, the Wistar male rats (170 to 220 g) were used.

If the animal is entered in the big box, the animal has the tendency to immediately enter into the small box. When the animal entered in the small box, the door was closed and then the electric current was passed through the metal grid (3mA, 5 seconds). If the same animal was entered in the big box 3 or more hours later, the animal entered into the small box not immediately, but very later. That is, the latency until the animal enters from the big box into the small box was prolonged. This reaction is generally called as "passive avoidance response".

After the electric current was passed through the metal grid and then the electroconvulsive shock was given to the animal by passing the electric current through the electrodes put on both ears of the animal (60 mA, 200 Hz, 0.8 second), the passive avoidance response was checked 3 or more hours later. The reduction in latency was observed. This reduction in latency is due to the forgetting of the electric stimulus by giving the electroconvulsive shock and it is used as the index of the impairments of memory.

Further, after the electroconvulsive shock was given and then the compound to be tested (the present compounds and the nootropic agents) was orally administrated so as to improve the impairment of memory, the passive avoidance response was checked 3 or more hours later, again. The prolongation of the latency reduced by electroconvulsive shock was observed by administrating each compound and it is used as the index of the improvement of the impairment of memory.

The improvement (%) using each compound was calculated from the following equation:

$$\text{improvement (\%)} = \frac{T - I}{C - I} \times 100$$

wherein
  C is the latency to enter small box in the control group;
  I is the latency to enter small box in the impaired group; and
  T is the latency to enter small box in the treating group.

The results are shown in Table 2.

TABLE 2

| Compound (Example No.) | Dose (mg/kg, P.O.) | improvement (%) |
| --- | --- | --- |
| 1 | 5 | 23.2 |
|   | 10 | 47.6 |
| 2 | 10 | 11.7 |
|   | 100 | 26.8 |
|   | 300 | 19.6 |
| 6 | 10 | 8.0 |
|   | 30 | 13.7 |
|   | 100 | 26.5 |
| 7 | 1 | 23.0 |
|   | 10 | 28.1 |
| Piracetam | 250 | 22.0 |
|   | 500 | 14.0 |
| Aniracetam | 30 | 0 |
|   | 60 | 0 |
|   | 100 | 21.0 |

TEST EXAMPLE 2

Effect on NaNo$_2$ induced behavioral disturbance in the tight rope test

The test was carried out in accordance with the method of Gary E. Gibson (please see Pharmacology, Biochemistry & Behavior, 18, pages 909 to 916, 1983).

As the experimental animal, the ddy male mice (20 to 25 g, 6 mice per group) were used.

Firstly, the animals in the control group were subjected to the tight rope test. The tight rope test was carried out as follows. The rope having the diameter of about 2 mm and the length of about 60 cm was stretched tightly between the poles having the height of about 40 cm. The animal was held on the middle of the rope with the forelimbs and the time till the animal arrives to any pole was determined. The time limit is set within 1 minute. And, the behavior during the course was observed so as to score according to Gibson method above.

Next, 150 mg/kg of sodium nitrate was intraperitoneally administered and 30 minutes later the animal was subjected to the tight rope test. It has been known that the animal was caused to be the anemic hypoxia and have the lowered capacity of acetylcholine synthesis by administrating sodium nitrite, thereby the score on the tight rope test being lowered.

After the administration of sodium nitrite, 30 minutes later the compound to be tested (the present compounds and the nootropic agents) was orally administered so as to improve the lowered capacity of acetylcholine synthesis and possibly the impaired brain function and further 30 minutes later the animal was subjected to the tight rope test, again. The increase with respect to the score was observed by administrating each compound.

The improvement (%) using each compound was calculated from the following equation:

$$\text{improvement (\%)} = \frac{T - I}{C - I} \times 100$$

wherein
C is the mean score in the control group;
I is the mean score in the impaired group; and
T is the mean score in the treating group.
The results are shown in Table 3.

TABLE 3

| Compound (Example No.) | Dose (mg/kg, P.O.) | improvement (%) |
| --- | --- | --- |
| 1 | 6.25 | 20.3 |
|   | 12.5 | 36.4 |
|   | 25 | 24.6 |
|   | 50 | 20.5 |
|   | 100 | 64.3 |
|   | 200 | 60.5 |
| 2 | 0.02 | 15.5 |
|   | 1.0 | 59.0 |
|   | 25 | 0 |
|   | 50 | 26.8 |
| 6 | 10 | 28.7 |
|   | 30 | 20.4 |
|   | 100 | 33.3 |
| 7 | 3 | 52.7 |
|   | 10 | 23.6 |
|   | 30 | 5.5 |
| Piracetam | 30 | 14.9 |
|   | 100 | 29.9 |
|   | 300 | 38.8 |
| Aniracetam | 30 | 31.0 |
|   | 100 | 7.8 |
|   | 300 | 0 |

EFFECT OF THE INVENTION

The present compounds are useful as the agents for improving the impaired brain function.

What is claimed is:

1. 4-Piperidinecarboxamide derivatives represented by the general formula (I):

wherein each $R^1$ and $R^2$ represents a hydrogen atom, or $R^1$ together with $R^2$ represents a cyclopentanespiro or cyclohexanespiro group; $R^3$ represents a hydrogen atom, an alkyl group having 1 to 4 carbon atoms, an aralkyl group or an indolylalkyl group; and n is an integer of 1 or 2.

2. The compound according to claim 1, wherein $R^3$ in the general formula (I) represents a hydrogen atom, a methyl group, an isopropyl group, a benzyl group or an indole-3-yl-methyl group.

3. A pharmaceutical composition useful as the agent for improving the impaired brain function comprising as the effective ingredient at least one of 4-piperidinecarboxamide derivatives represented by the general formula (I):

wherein each $R^1$ and $R^2$ represents a hydrogen atom, or $R^1$ together with $R^2$ represents a cyclopentanespiro or cyclohexanespiro group; $R^3$ represents a hydrogen atom, an alkyl group having 1 to 4 carbon atoms, an aralkyl group or an indolylalkyl group; and n is an integer of 1 or 2.

* * * * *